US011896427B2

(12) United States Patent
Du et al.

(10) Patent No.: US 11,896,427 B2
(45) Date of Patent: Feb. 13, 2024

(54) ULTRASONIC IMAGING APPARATUS AND METHOD FOR DETECTING SHEAR INDEX OF VASCULAR WALL USING ULTRASONIC WAVES (71) Applicant: SHENZHEN MINDRAY BIO-MEDICAL ELECTRONICS CO., LTD., Guangdong (CN)

(72) Inventors: Yigang Du, Shenzhen (CN); Yingying Shen, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 870 days.

(21) Appl. No.: 16/608,625

(22) PCT Filed: Apr. 28, 2017

(86) PCT No.: PCT/CN2017/082480
§ 371 (c)(1),
(2) Date: Jan. 19, 2021

(87) PCT Pub. No.: WO2018/195944
PCT Pub. Date: Nov. 1, 2018

(65) Prior Publication Data
US 2021/0236086 A1 Aug. 5, 2021

(51) Int. Cl.
*A61B 8/08* (2006.01)
*A61B 8/06* (2006.01)
(Continued)

(52) U.S. Cl.
CPC .............. *A61B 8/0891* (2013.01); *A61B 8/06* (2013.01); *A61B 8/14* (2013.01); *A61B 8/461* (2013.01); *A61B 8/485* (2013.01)

(58) Field of Classification Search
CPC .......... A61B 8/0891; A61B 8/06; A61B 8/14; A61B 8/461; A61B 8/485; A61B 8/467; A61B 8/469; A61B 8/5223
See application file for complete search history.

(56) References Cited

U.S. PATENT DOCUMENTS 9,259,205 B2    2/2016  Tanaka et al.
9,349,178 B1*   5/2016  Itu ..................... A61B 6/5217
(Continued)

FOREIGN PATENT DOCUMENTS

CN   101474083 A   7/2009
CN   103327904 A   9/2013
(Continued)

OTHER PUBLICATIONS

Tomasz A. Kowalewski, Lecture Notes 6, Blood Flow Modelling and Diagnostics, Institute of Fundamental Technological Research, Polish Academy of Sciences, Warsaw, Poland, 2005.*

(Continued)

*Primary Examiner* — Bo Joseph Peng
(74) *Attorney, Agent, or Firm* — Sheppard Mullin Richter & Hampton LLP (57) ABSTRACT An ultrasonic imaging apparatus, a method for detecting a shear index of a vascular wall using ultrasonic waves, and a computer readable storage medium are provided. The method comprises: transmitting ultrasonic waves to an region of interest comprising a vessel; receiving the ultrasonic waves to obtain echo signals; acquiring an ultrasonic image according to the echo signals; acquiring particle jet velocities of a plurality of points in the vessel, the particle jet velocity comprising flow velocity and flow direction; determining a vascular wall in the ultrasonic image; acquiring a position to be detected of the vascular wall; calculating, according to particle jet velocities of a plurality of points near the position to be detected, the shear index of the (Continued)

position to be detected of the vascular wall; and displaying the ultrasonic image and the shear index of the vascular wall.

20 Claims, 7 Drawing Sheets (51) Int. Cl.
*A61B 8/14* (2006.01)
*A61B 8/00* (2006.01)

(56) References Cited

U.S. PATENT DOCUMENTS

| | | | |
|---|---|---|---|
| 2008/0015440 A1* | 1/2008 | Shandas | A61B 8/13 600/458 |
| 2008/0269611 A1* | 10/2008 | Pedrizzetti | G01S 7/52071 382/128 |
| 2009/0014360 A1* | 1/2009 | Toner | B01D 21/0087 209/208 |
| 2012/0095332 A1 | 4/2012 | Nitta et al. | |
| 2012/0265075 A1* | 10/2012 | Pedrizzetti | A61B 8/06 600/454 |
| 2014/0316758 A1* | 10/2014 | Yagi | A61B 5/026 703/9 |
| 2015/0141832 A1* | 5/2015 | Yu | A61B 8/488 600/455 |
| 2018/0085088 A1 | 3/2018 | Du et al. | |
| 2019/0192111 A1* | 6/2019 | Shimizu | A61B 8/463 |
| 2020/0126219 A1* | 4/2020 | Wang | A61B 8/463 |

FOREIGN PATENT DOCUMENTS

| | | |
|---|---|---|
| CN | 104116563 A | 10/2014 |
| CN | 105708495 A | 6/2016 |
| CN | 106102589 A | 11/2016 |
| JP | 2016-131836 A | 7/2016 |
| WO | 2014/190541 A1 | 12/2014 |

OTHER PUBLICATIONS

PCT International Search Report and the Written Opinion dated Jan. 25, 2018, issued in related International Application No. PCT/CN2017/082480 (11 pages).

PCT International Preliminary Report on Patentability dated Nov. 7, 2019, issued in related International Application No. PCT/CN2017/082480, with English machine translation (13 pages).

First Search dated Aug. 22, 2020, issued in related Chinese Application No. 201780018341.3 (2 pages).

First Office Action dated Sep. 1, 2020, issued in related Chinese Application No. 201780018341.3, with English machine translation (19 pages).

Yuanxing Zhang et al., "Effect of shear force on biological response", Chapter VII, Section I, p. 122, Oct. 31, 2001, The East China University of Science and Technology Press, Bioreactor Engineering.

* cited by examiner

ULTRASONIC IMAGING APPARATUS AND METHOD FOR DETECTING SHEAR INDEX OF VASCULAR WALL USING ULTRASONIC WAVES

CROSS-REFERENCE TO RELATED PATENT APPLICATION

This application is a U.S. National Stage Application under 35 U.S.C. 371 of International Patent Application No. PCT/CN2017/082480, filed on Apr. 28, 2017, the content of the above-identified application is incorporated herein by reference in its entirety in the present disclosure.

TECHNICAL FIELD

The present disclosure relates to imaging method, in particular to ultrasonic imaging apparatuses and methods for detecting a vascular wall shear index using ultrasonic waves used in the ultrasonic imaging apparatuses.

BACKGROUND

A vascular wall shear index, such as WSS (Wall Shear Stress), is a parameter related to arteriosclerosis known in medicine. The vascular wall shear index is usually related to the gradient of the flow velocity component in the tangential direction of the vascular wall near the vascular wall. Therefore, when calculating or detecting the WSS value, the magnitude and direction of the flow velocity in the vessel need to be known first, so as to obtain its component value in the tangential direction of the vascular wall. In a traditional detection method, the color Doppler ultrasonic imaging method using Doppler principle is used. However, what is obtained by this method is the component of the flow velocity in the ultrasonic propagation direction, and it is difficult for this method to obtain the component of the flow velocity in the tangential direction of the vascular wall. Therefore, this method based on traditional color Doppler ultrasonic imaging cannot accurately obtain the WSS, but can only make qualitative analysis on WSS. In another traditional detection method, the phase-contrast magnetic resonance angiography (PC-MRA) is used to obtain the magnitude and direction of flow velocity to calculate the WSS. However, the method based on the phase-contrast magnetic resonance angiography will spend a long inspection time, must use expensive equipments, and will bring a lot of inconvenience to patients and doctors during the inspection. For example, it will lead to poor inspection comfort, require ECG (Electrocardiograph) calibration, and undergo interference to the signals, and so on.

SUMMARY

Therefore, the present disclosure provides an ultrasonic imaging apparatus and a method for detecting the vascular wall shear index using ultrasonic waves, which can accurately detect the vascular wall shear index at a lower cost.

In one embodiment of the present disclosure, an ultrasonic imaging apparatus may include a probe, a transmitting circuit, a receiving circuit and a processor. The transmitting circuit may be configured to excite the probe to transmit ultrasonic waves to a region of interest containing a vessel. The receiving circuit may be configured to receive echo signals generated after the transmitting of the ultrasonic waves. The processor may be configured to obtain an ultrasonic image of the region of interest according to the echo signals; obtain particle jet velocities at multiple points in the vessel according to the echo signals, where the particle jet velocity include a magnitude and a direction of a flow velocity; determine a vascular wall in the ultrasonic image and obtain a measurement position on the vascular wall; calculate a vascular wall shear index at the measurement position according to the particle jet velocities at a plurality of points near the measurement position; and displaying the ultrasonic image and the vascular wall shear index on a display device.

In one embodiment, the ultrasonic waves transmitted to the region of interest containing the vessel by the probe excited by the transmitting circuit may include multiple first ultrasonic wave with multiple steering angles transmitted in a multi-steering angle transmitting mode, and the processor may, according to first echo signals in the multiple steering angles at the multiple points received by the receiving circuit, respectively obtain velocity components in the multiple steering angles at each point of the multiple points and recover a particle jet velocity from the velocity components in the multiple steering angles at each point of the multiple points to obtain the particle jet velocities at the multiple points.

In one embodiment, the ultrasonic waves transmitted to the region of interest containing the vessel by the probe excited by the transmitting circuit may further include a second ultrasonic wave, and the image generating module may generate the ultrasonic image according to a second echo signal obtained by the receiving circuit receiving echoes of the second ultrasonic wave. The first ultrasonic wave may be different from the second ultrasonic wave.

In one embodiment, the processor may be configured to calculate the vascular wall shear index at the measurement position according to the particle jet velocities at the plurality of points near the measurement position by determining a tangential direction of the vascular wall at the measurement position, obtaining the particle jet velocities at the plurality of points near the measurement position, calculating velocity components of the particle jet velocities at the plurality of points in the tangential direction, and obtaining the vascular wall shear index at the measurement position according to the calculated plurality of velocity components.

In one embodiment, the processor may be configured to determine the tangential direction of the vascular wall at the measurement position by, in response to an adjustment to the vascular wall identifier, determining a direction of a tangential marker used to indicate the tangential direction in the adjusted vascular wall identifier to be the tangential direction of the vascular wall.

In one embodiment, the processor may be configured to determine the vascular wall at the vessel detection position in response to a vascular wall identifier added on the ultrasonic image.

In one embodiment, the processor may be configured to obtain an area in the ultrasonic image in which a brightness is higher than a preset brightness threshold and determine the area in which the brightness is higher than the preset brightness to be the vascular wall.

In one embodiment, the processor may be configured to calculate a flow energy at a vessel detection position, search for an edge of the flow energy, obtain an area in the ultrasonic image in which a brightness is higher than a preset brightness threshold and which is located at the edge of the flow energy, and determine the area in which the brightness is higher than the preset brightness threshold and which is located at the edge of the flow energy to be the vascular wall.

In one embodiment, the processor may be further configured to compare the flow energy with an energy threshold and determine a position where the flow energy is lower than the energy threshold to be a position of the edge of the flow energy.

In one embodiment, the vascular wall shear index may include a velocity gradient, and the processor may be further configured to obtain derivatives of the plurality of velocity components with a normal radius of the vascular wall at current measurement position to obtain the velocity gradient.

In one embodiment, the vascular wall shear index may further include a wall shear stress, and the processor may be further configured to calculate a product of a flow viscosity coefficient and the velocity gradient to obtain the wall shear stress.

In one embodiment, the vascular wall shear index may further include an oscillatory shear index, and the processor may further be configured to calculate the oscillatory shear index according to an integral of the wall shear stress in one cardiac cycle.

In one embodiment, the processor may further be configured to display the particle jet velocities at the multiple points in the vessel on the ultrasonic image after the analysis module obtains the particle jet velocities at the multiple points in the vessel according to the echo signals.

In one embodiment, the vascular wall shear index may include a velocity gradient, a wall shear stress and/or an oscillatory shear index, and the processor may display the ultrasonic image and the vascular wall shear index on the display device by: displaying the velocity gradient, the wall shear stress and/or the oscillatory shear index of the vascular wall at at least one measurement position separately or simultaneously through a map on the display device.

In one embodiment, the processor may display a map of the value of the velocity gradient, the value of the wall shear stress and/or the value of the oscillatory shear index of the vascular wall at one measurement position over time. Alternatively, the display control module may switch between displaying maps of the value of the velocity gradient, the value of the wall shear stress and/or the value of the oscillatory shear index of the vascular wall at multiple measurement positions at the current moment.

In one embodiment, the processor may further be configured to display a position with a maximum or minimum velocity gradient, wall shear stress and oscillatory shear index in the vascular wall at the at least one measurement position and the values of the corresponding maximum or minimum velocity gradient, wall shear stress and oscillatory shear index.

In one embodiment, the processor may further be configured to determine a vessel bifurcation position according to the ultrasonic image and display the velocity gradient, the wall shear stress and/or the oscillatory shear index at the vessel bifurcation position.

In one embodiment, the processor may further be configured to determine center lines of the vessels in the region of interest according to the ultrasonic image and determine a position where multiple center lines intersect to be the vessel bifurcation position.

In one embodiment, the ultrasonic image may be a two-dimensional image or a three-dimensional image.

In one embodiment of the present disclosure, a method for detecting the vascular wall shear index using ultrasonic waves is provided, which may include: transmitting ultrasonic waves to a region of interest containing a vessel; receiving echoes to obtain echo signals, obtaining an ultrasonic image according to the echo signals; obtaining particle jet velocities at multiple points in the vessel according to the echo signals, where the particle jet velocity comprises a magnitude and a direction of a flow velocity; determining a vascular wall in the ultrasonic image; obtaining a measurement position on the vascular wall; calculating the vascular wall shear index at the measurement position according to the particle jet velocities at a plurality of points near the measurement position; and displaying the ultrasonic image and the vascular wall shear index.

In one embodiment, the step of transmitting the ultrasonic waves to the region of interest containing the vessel may include transmitting multiple first ultrasonic waves with multiple steering angles to a scan target in a multi-steering angle transmitting mode. The step of obtaining the particle jet velocities at the multiple points in the vessel according to the echo signals may include: according to first echo signals in the multiple steering angles at the multiple points received by the receiving circuit, respectively obtaining velocity components in the multiple steering angles at each point of the multiple points and recovering a particle jet velocity from the velocity components in the multiple steering angles at each point of the multiple points to obtain the particle jet velocities at the multiple points.

In one embodiment, the step of transmitting the ultrasonic waves to the region of interest containing the vessels may further include transmitting a second ultrasonic wave to the region of interest containing the vessels. The step of obtaining the ultrasonic image according to the echo signals may include receiving echoes of the second ultrasonic wave to obtain second echo signals and obtaining the ultrasonic image according to the second echo signals. The first ultrasonic waves may be different from the second ultrasonic wave.

In one embodiment, the step of calculating the vascular wall shear index at the measurement position according to the particle jet velocities at the plurality of points near the measurement position may include: determining a tangential direction of the vascular wall at the measurement position; obtaining the particle jet velocities at the plurality of points near the measurement position; calculating velocity components of the particle jet velocities at the plurality of points in the tangential direction; and obtaining the vascular wall shear index at the measurement position according to the calculated plurality of velocity components.

In one embodiment, the step of determining the tangential direction of the vascular wall may include, in response to an adjustment to a vascular wall identifier, determining a direction of a tangential marker used to indicate the tangential direction in the adjusted vascular wall identifier to be the tangential direction of the vascular wall.

In one embodiment, the step of determining the vascular wall in the ultrasonic image may include determining the vascular wall at the vessel detection position in response to a vascular wall identifier added on the ultrasonic image.

In one embodiment, the step of determining the vascular wall in the ultrasonic image may include obtaining an area in the ultrasonic image in which a brightness is higher than a preset brightness threshold and determining the area in which the brightness is higher than the preset brightness to be the vascular wall.

In one embodiment, the step of determining the vascular wall in the ultrasonic image may include: calculating a flow energy at a vessel detection position; searching for an edge of the flow energy; and obtaining an area in the ultrasonic image in which a brightness is higher than a preset brightness threshold and which is located at the edge of the flow energy, and determine the area in which the brightness is higher than the preset brightness threshold and which is located at the edge of the flow energy to be the vascular wall.

In one embodiment, the step of searching for the edge of the flow energy may include: comparing the flow energy with an energy threshold and determining a position where the flow energy is lower than the energy threshold to be a position of the edge of the flow energy.

In one embodiment, the vascular wall shear index may include a velocity gradient, and the step of calculating the vascular wall shear index at the measurement position according to the particle jet velocities at the plurality of points near the measurement position may include obtaining derivatives of the plurality of velocity components with a normal radius of the vascular wall at current measurement position.

In one embodiment, the vascular wall shear index may further include a wall shear stress, and the step of calculating the vascular wall shear index at the measurement position according to the particle jet velocities at the plurality of points near the measurement position may further include calculating a product of a flow viscosity coefficient and the velocity gradient to obtain the wall shear stress.

In one embodiment, the vascular wall shear index may further include an oscillatory shear index, and the step of calculating the vascular wall shear index at the measurement position according to the particle jet velocities at the plurality of points near the measurement position may further include calculating the oscillatory shear index according to an integral of the wall shear stress in one cardiac cycle.

In one embodiment, after obtaining the particle jet velocities at multiple points in the vessel according to the echo signals, the method may further include displaying the particle jet velocities at the multiple points in the vessel on the ultrasonic image.

In one embodiment, the vascular wall shear index may include a velocity gradient, a wall shear stress and/or an oscillatory shear index, and the step of displaying the ultrasonic image and the vascular wall shear index may include displaying the velocity gradient, the wall shear stress and/or the oscillatory shear index of the vascular wall at at least one measurement position separately or simultaneously through a map.

In one embodiment, the step of displaying the velocity gradient, the wall shear stress and/or the oscillatory shear index of the vascular wall at the at least one measurement position separately or simultaneously through the map may include: displaying a map of the value of the velocity gradient, the value of the wall shear stress and/or the value of the oscillatory shear index of the vascular wall at one measurement position over time, or switching between displaying maps of the value of the velocity gradient, the value of the wall shear stress and/or the value of the oscillatory shear index of the vascular wall at multiple measurement positions at the current moment.

In one embodiment, the method may further include displaying a position with a maximum or minimum velocity gradient, wall shear stress and oscillatory shear index in the vascular wall at the at least one measurement position and the values of the corresponding maximum or minimum velocity gradient, wall shear stress and oscillatory shear index.

In one embodiment, the method may further include determining a vessel bifurcation position according to the ultrasonic image; and displaying the velocity gradient, the wall shear stress and/or the oscillatory shear index at the vessel bifurcation position.

In one embodiment, the step of determining the vessel bifurcation position according to the ultrasonic image may include determining center lines of vessels in the region of interest according to the ultrasonic image and determining a position where multiple center lines intersect to be the vessel bifurcation position.

In one embodiment, the ultrasonic image may be a two-dimensional image or a three-dimensional image.

In one embodiment of the present disclosure, a method for detecting the vascular wall shear index using ultrasonic waves is provided, which may include: transmitting ultrasonic waves to a region of interest containing a vessel; receiving echoes to obtain echo signals; obtaining an ultrasonic image according to the echo signals; obtaining particle jet velocities at multiple points in the vessel according to the echo signals, where the particle jet velocity comprises a magnitude and a direction of a flow velocity; determining a vascular wall and a measurement position in the ultrasonic image; calculating the vascular wall shear index at the measurement position according to the particle jet velocities at a plurality of points near the measurement position of the vascular wall; generating an index mark, wherein an attribute of the index mark corresponds to a calculated value of the vascular wall shear index; and displaying the index mark corresponding to the measurement position at the measurement position on the vascular wall.

In one embodiment of the present disclosure, a computer-readable storage medium storing a plurality of program instructions is provided. The plurality of program instructions may be called by a processor to implement the methods above, which may at least include: transmitting ultrasonic waves to a region of interest containing a vessel; receiving echoes to obtain echo signals, obtaining an ultrasonic image according to the echo signals; obtaining particle jet velocities at multiple points in the vessel according to the echo signals, where the particle jet velocity comprises a magnitude and a direction of a flow velocity; determining a vascular wall in the ultrasonic image; obtaining a measurement position on the vascular wall; calculating the vascular wall shear index at the measurement position according to the particle jet velocities at a plurality of points near the measurement position; and displaying the ultrasonic image and the vascular wall shear index.

In one embodiment of the present disclosure, a computer-readable storage medium storing a plurality of program instructions is provided. The plurality of program instructions may be called by a processor to implement the methods above, which may include: transmitting ultrasonic waves to a region of interest containing a vessel; receiving echoes to obtain echo signals; obtaining an ultrasonic image according to the echo signals; obtaining particle jet velocities at multiple points in the vessel according to the echo signals, where the particle jet velocity comprises a magnitude and a direction of a flow velocity; determining a vascular wall and a measurement position in the ultrasonic image; calculating the vascular wall shear index at the measurement position according to the particle jet velocities at a plurality of points near the measurement position of the vascular wall; generating an index mark, wherein an attribute of the index mark corresponds to a calculated value of the vascular wall shear index; and displaying the index mark corresponding to the measurement position at the measurement position on the vascular wall.

In the ultrasonic imaging apparatuses, the methods for detecting the vascular wall shear index using ultrasonic waves and the computer-readable storage medium of the present disclosure, the vascular wall shear index at the measurement position may be calculated by obtaining the particle jet velocities at a plurality of points near the measurement position on the vascular wall, which is low cost and accurate detection.

BRIEF DESCRIPTION OF THE DRAWINGS

In order to more clearly illustrate the technical solutions in the embodiments of the present disclosure, the drawings used in the embodiments will be briefly described below. Obviously, the drawings below are only several embodiments of the present disclosure. Those ordinarily skilled in the art can obtain other drawings according to the drawings without paying creative labor.

DETAILED DESCRIPTION

The technical solutions in the embodiments of the present disclosure will be clearly and completely described with reference to the drawings below. Obviously, the described embodiments are only a part of the embodiments of the present disclosure, but not all of them. All other embodiments obtained by those ordinarily skilled in the art based on the embodiments of the present disclosure without creative efforts shall fall within the protection scope of the present disclosure.

Figure 1:
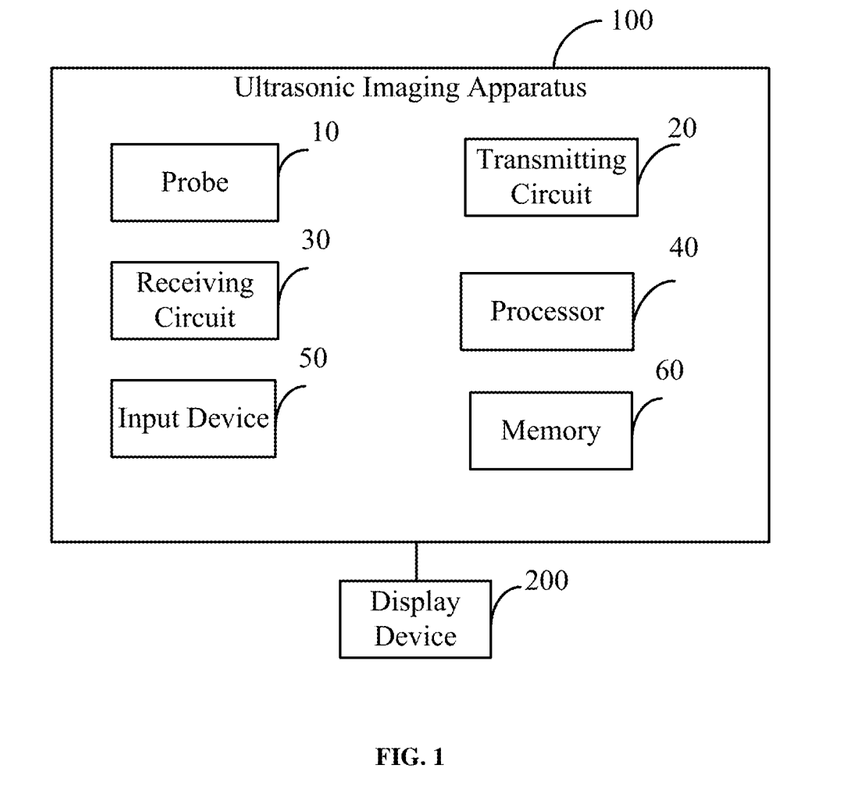
FIG. 1 is a block diagram of an ultrasonic imaging apparatus in one embodiment of the present disclosure.

Referring to FIG. 1, which is a block diagram of an ultrasonic imaging apparatus 100 in one embodiment of the present disclosure, the ultrasonic imaging apparatus 100 may include a probe 10, a transmitting circuit 20, a receiving circuit 30, and a processor 40. The probe 10 may be used to directly or indirectly contact a region of interest 200 to be examined. In some embodiments, the region of interest 200 to be examined is a region of interest 200 containing vascular tissue. The transmitting circuit 20 may be configured to excite the probe 10 to transmit ultrasonic waves to the region of interest 200 including vascular tissue. The receiving circuit 30 may be configured to receive echo signals generated after the transmitting of the ultrasonic waves.

The processor 40 may be connected with the transmitting circuit 20 and the receiving circuit 30.

The processor 40 may be configured to obtain an ultrasonic image of the region of interest according to the echo signals received by the receiving circuit 30, where an image generating module 401 may generate the ultrasonic image of the region of interest according to waveform parameters or the like of the echo signals.

The processor 40 may further be configured to obtain the particle jet velocities at multiple points in the vessel in the region of interest 200 containing the vascular tissue according to the echo signals received by the receiving circuit 30. The particle jet velocity may include the magnitude and direction of the flow velocity. The particle jet velocity may be the actual velocity of the flow and represent the true direction and magnitude of the flowing flow in the vessel.

The processor 40 may be configured to determine a vascular wall in the ultrasonic image, and obtain a measurement position on the vascular wall.

The processor 40 may further be configured to calculate a vascular wall shear index at the measurement position according to the particle jet velocities at multiple points near the measurement position.

After calculating the vascular wall shear index at the measurement position, the processor 40 may further be configured to control a display device 200 to display the ultrasonic image and the vascular wall shear index. In some embodiments, the display device 200 may be an external display device, such as a liquid crystal display, etc., which is connected to the ultrasonic imaging apparatus 100 in a wired or wireless manner. In some embodiments, the display device 200 may be a display screen integrated in the ultrasonic imaging apparatus 100, such as a touch screen.

In some embodiments, the transmitting circuit 20 exciting the probe 10 to transmit ultrasonic waves to the region of interest 200 containing the vascular tissue may include: the transmitting circuit 20 exciting the probe 10 to transmit multiple first ultrasonic waves steered in multiple steering angles to the region of interest 20 containing the vascular tissue in a multi-steering angle transmitting mode. The processor may be configured to respectively obtain the velocity components in the multiple steering angles at each point of multiple points according to first echo signals at the multiple points in the multiple steering angles received by the receiving circuit 30, and recover the particle jet velocity from the obtained velocity components in the multiple steering angles at each point of the multiple points, thereby obtaining the particle jet velocities at the multiple points.

That is, when the transmitting circuit 20 excites the probe 10 to transmit multiple first ultrasonic waves steered in multiple steering angles to the region of interest 20 containing the vascular tissue in a multi-steering angle transmitting mode, the first echo signals received by the receiving circuit 30 will include the echo signals reflected from multiple points, and the echo signals reflected from each point will include echo signals reflected in multiple steering angles. The processor may obtain the velocity components at each point of the multiple points in the multiple steering angles according to the multiple echo signals reflected in the multiple steering angles from each point of the multiple points, and recover the particle jet velocity at said point from the obtained velocity components in different angles at said point, so as to obtain the particle jet velocities at the multiple points. When transmitting the multiple first ultrasonic waves in the multiple steering angles, the steering angle may refer to the deflection angle between the transmitting direction of the ultrasonic waves and the normal of the end face of the ultrasonic probe. For example, for a matrix ultrasonic probe, the steering angle may be the deflection angle between the transmitting direction and the normal of the end face of the ultrasonic probe in the three-dimensional space. The velocity component corresponding to each steering angle may be obtained using a conventional Doppler velocity calculation method.

Figure 2:
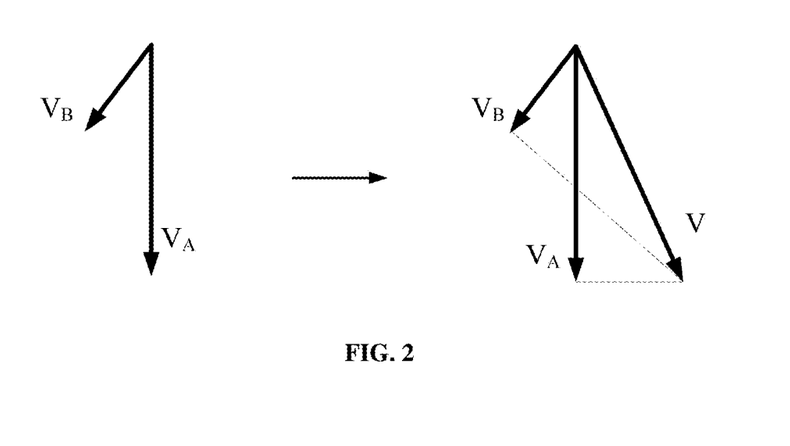
FIG. 2 is a schematic diagram of recovering from the velocity components in different angles in one embodiment of the present disclosure.

FIG. 2 is a schematic diagram of recovering from the velocity components in different angles. In FIG. 2, only an example of recovering from velocity components in two angles is shown. Assuming that the velocity component in one angle at a certain point is VA and the velocity component in the other angle is VB, the particle jet velocity at the point obtained by the recovering will be V. Since in the case that there exist the first echo signals in multiple steering angles the corresponding velocity components in the multiple steering angles will be in different planes, the velocity components VA and VB and the particle jet velocity will be in different planes. Therefore, FIG. 2 shows the schematic diagram of the recovering of VA and VB in three-dimensional space.

In other embodiments, the transmitting circuit 20 exciting the probe 10 to transmit the ultrasonic waves to the region of interest 200 containing the vascular tissue may further include transmitting a second ultrasonic wave to the region of interest 200 containing the vascular tissue. The second ultrasonic wave may be different from the first ultrasonic wave, and may be transmitted after or before the first ultrasonic wave.

The receiving circuit 30 may receive the echo signals of the second ultrasonic wave to obtain second echo signals. That is, the receiving circuit 30 may receive the second echo signals generated by the region of interest containing the vessel in response to the second ultrasonic wave.

The processor 40 may specifically be configured to obtain the ultrasonic image of the region of interest according to the second echo signals received by the receiving circuit 30. The second ultrasonic wave may an ultrasonic wave used to generate an ultrasonic image, and may be the same as an existing ultrasonic wave used to generate an ultrasonic image.

In some embodiments, the first ultrasonic wave and the second ultrasonic wave may be the same ultrasonic waves and transmitted to obtain the echo signals. A part of the echo signals may be used to generate the ultrasonic image, while a part or all of the echo signals may be used to calculate the particle jet velocities at multiple points in the vessel. For example, the first ultrasonic wave and the second ultrasonic wave may be one of diverged waves, plane waves, and weakly focused waves, etc., or the combination thereof. In another embodiment, the first ultrasonic wave and the second ultrasonic wave may be different ultrasonic waves with different types, and be respectively transmitted in an transmitting sequence to obtain the echo signals. The echo signals corresponding to the transmitted second ultrasonic wave may be used to obtain the ultrasonic image, while the echo signals corresponding to the transmitted first ultrasonic wave may be used to obtain the particle jet velocities. For example, the first ultrasonic wave may be one of diverged waves, plane waves, and weakly focused waves, etc., or the combination thereof. The second ultrasonic wave may be focused waves, so as to obtain the ultrasonic image with better quality.

In addition, besides the recovering of the velocity components in multiple angles, a speckle tracking method may also be used to obtain the particle jet velocities at multiple points in the vessel according to the ultrasonic echo signals, as shown below.

For example, in one embodiment of the present disclosure, obtaining the particle jet velocities at multiple points in the vessel according to the ultrasonic echo signals may include the following steps.

First, at least two frames of image data may be obtained according to the obtained ultrasonic echo signals. For example, at least first frame of image data and second frame of image data may be obtained. As described above, in this embodiment, plane ultrasonic beams may be used to obtain the image data used for calculating the particle jet velocities at target points. The plane ultrasonic beam propagates substantially in the entire imaging area. Therefore, usually, one plane beam echo signal obtained by transmitting the plane ultrasonic beam one time may be processed to obtain one frame of plane beam echo image data. In the present disclosure, the ultrasonic image data of the scanning target obtained by correspondingly processing the plane beam echo signal corresponding to the plane ultrasonic beam is referred to as "plane beam echo image data".

Thereafter, a tracking area may be selected in the first frame of image data. The tracking area may contain a target points where the velocity vector is desired to be obtained. For example, the tracking area may be a neighborhood of the target point or a data block containing the target point.

Next, a region corresponding to the tracking area may be searched in the second frame of image data. For example, a region having the greatest similarity to the tracking area may be searched as a tracking result area. Here, the similarity may be measured using a measurement method generally used in the art.

Finally, according to the positions of the tracking area and the tracking result area and the time interval between the first frame of image data and the second frame of image data, the particle jet velocity at the target point may be obtained. For example, the magnitude of the particle jet velocity may be determined by dividing the distance between the tracking area and the tracking result area (that is, the displacement of the target point within a preset time interval) by the time interval between the first frame of plane beam echo image data and the second frame of plane beam echo image data, and the direction of the particle jet velocity may be the direction of the line from the tracking area to the tracking result area, that is, the moving direction of the target point within the preset time interval.

In some embodiments, the processor 40 calculating the vascular wall shear index at the measurement position according to the particle jet velocities at the multiple points near the measurement position may include: the processor 40 determining a tangential direction of the vascular wall at the measurement position, obtaining the particle jet velocities at the multiple points near the measurement position, calculating the velocity components of the particle jet velocities at the multiple points in the tangential direction, and obtaining the vascular wall shear index at the measurement position according to the calculated plurality of velocity components.

In some embodiment, the processor 40 determining the vascular wall in the ultrasonic image may include the processor 40 determining the vascular wall of the vessel to be detected in response to a vascular wall identifier added on the ultrasonic image.

As shown in FIG. 1, the ultrasonic imaging apparatus 100 may further include an input device 50. A user, for example, a doctor, may observe the ultrasonic image to confirm the position of the vascular wall in the ultrasonic image, and add the vascular wall identifier at the position of the vascular wall in the ultrasonic image through the input device 50.

Figure 3:
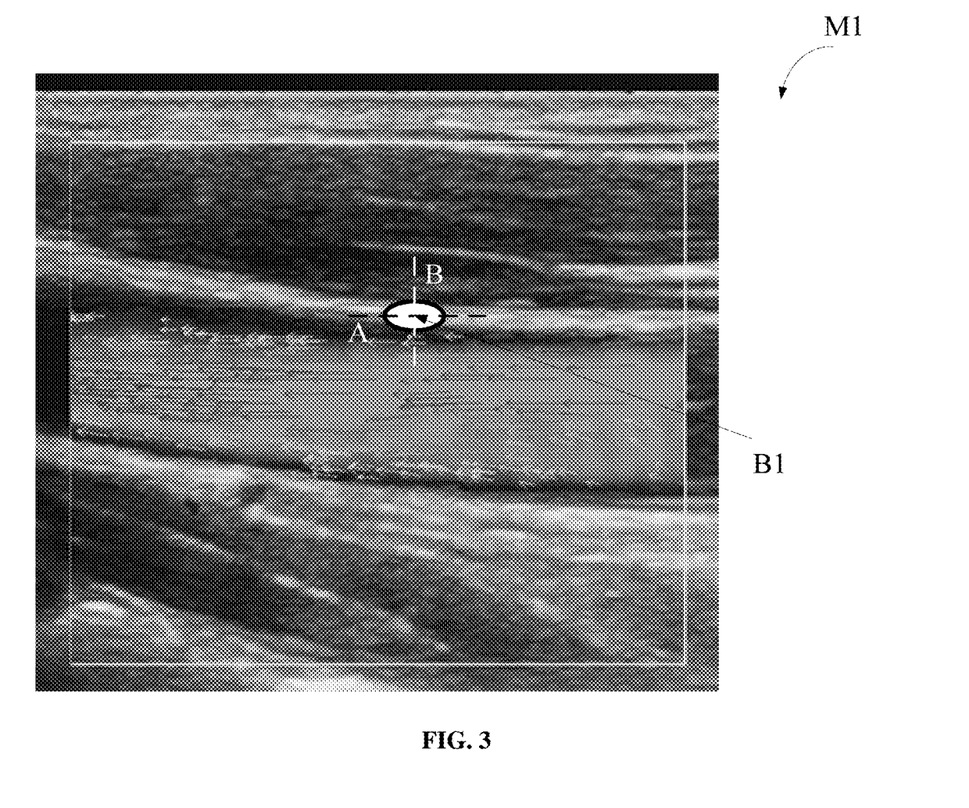
FIG. 3 is a schematic diagram of adding a vascular wall identifier to a vascular wall on an ultrasonic image in one embodiment of the present disclosure.

Reference may also be made to FIG. 3. As shown in FIG. 3, the user may add a vascular wall identifier B1 at the vascular wall observed on the ultrasonic image M1. As shown in FIG. 3, the vascular wall identifier B1 may further include two reference lines A and B that are perpendicular to each other. The reference line A is the black horizontal line shown in FIG. 3, and the reference line B is the white vertical line shown in FIG. 3.

The reference line A may be used to mark the direction of the vascular wall. The processor 40 determining the tangential direction of the vascular wall at the measurement position may include: changing the direction of the reference line A in response to a user's adjustment operation on the reference line B, and, after the adjustment operation is completed, determining the direction of the reference line A to be the tangential direction of the vascular wall at the measurement position. The positional relationship between the reference line A and reference line B may be relatively fixed, and adjustment of the reference line A will lead to the adjustment of the reference line B. In some embodiments, the vascular wall identifier B1 may have only the reference line A for identifying the direction of the vascular wall, and the reference line A may be directly adjusted to change the direction of the reference line A.

In another embodiment, the processor may also determine the vascular wall using an automatic identification method. For example, the processor 40 determining the vascular wall in the ultrasonic image may include: the processor 40 determining an area in the ultrasonic image in which the brightness is higher than a preset brightness threshold, and determining the area in which the brightness is higher than the preset brightness threshold to be the vascular wall. In another example, the processor 40 determining the vascular wall in the ultrasonic image may include: calculating the flow energy at a vessel detection position, searching for the edge of the flow energy, obtaining an area in the ultrasonic image in which the brightness is higher than the preset brightness threshold and which is located at the edge of the flow energy, and determining such area to be the vascular wall.

The processor 40 may compare the flow energy with an energy threshold, and determine the positions where the flow energy is lower than the energy threshold to be the position of the edge of the flow energy.

Since not all scanning region of the ultrasonic scanning contain the vessel, the determination based on single factor may be wrong. Adding the determination based on the flow energy, the accuracy of the determination can be significantly improved.

In some embodiments, the processor 40 may determine an area within a preset range of the vascular wall identifier B 1 added by the user as the measurement position. Alternatively, the processor 40 may automatically set the measurement position according to the obtained vascular wall. The measurement position here may be an area within one or more position ranges on the vascular wall, or an area within the position ranges of at least two segments arranged on the vascular wall.

In some embodiments, the vascular wall shear index may include a velocity gradient. The processor 40 calculating the vascular wall shear index at the measurement position according to the particle jet velocities at multiple points near the measurement position may include: the processor 40 obtaining the velocity gradients of the vascular wall by obtaining the derivative of the plurality of velocity components of the particle jet velocities at the multiple points with the normal radius of the vascular wall at the current measurement position. The velocity gradients may be values that change with time. Therefore, when displaying the velocity gradients, the velocity gradients displayed on the interface may change with time, so that the user can know the change of the velocity gradients in the entire observation time period.

In some embodiment, the velocity gradient of the vascular wall may be calculated according to a formula $$\left.\frac{\partial v_T}{\partial r}\right|_{r=R}.$$

In this formula, VT represents the velocity component, i.e. the component of the velocity in the tangential direction of the vascular wall. The velocity gradient may be obtained by deriving the velocity component at the normal radius r=R of the vascular wall.

Figure 4:
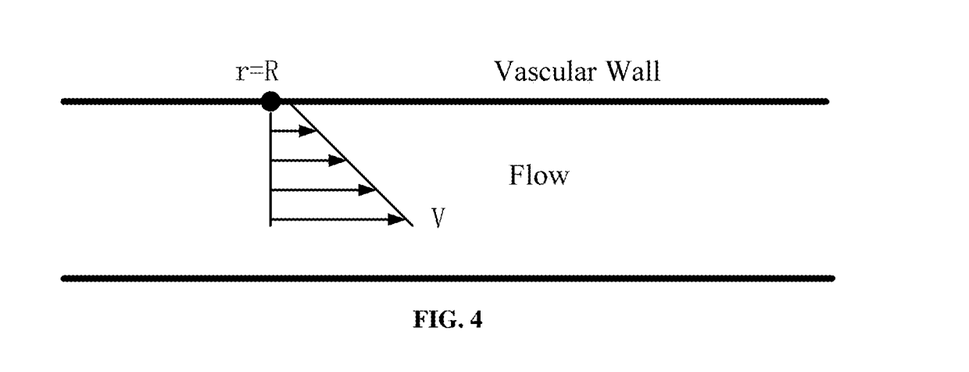
FIG. 4 is a schematic diagram of a velocity gradient of a vascular wall in one embodiment of the present disclosure.

Reference may also be made to FIG. 4, which is a schematic diagram of the velocity gradient of the vascular wall. As shown in FIG. 4, there may be plurality of velocity components in the tangential direction of the vascular wall at the current measurement position of the vascular wall. The velocity gradient of the vascular wall may be obtained by deriving the plurality of velocity components in the tangential direction of the vascular wall with the normal radius of the vascular wall at the current measurement position.

In some embodiments, the vascular wall shear index may further include the Wall Shear Stress (WSS), and the processor 40 may calculate the wall shear stress of the vascular wall by calculating a product of a flow viscosity coefficient and the obtained velocity gradient. The wall shear stress may be values that change with time. Therefore, when displaying the wall shear stress, the wall shear stress displayed on the interface may change with time, thereby enabling the user to understand the change of the wall shear stress during the entire observation period.

Specifically, the wall shear stress may be calculated according to a formula $$\tau = \mu \frac{\partial v_T}{\partial r}\bigg|_{r=R},$$

where τ represents the WSS (Wall Shear Stress), μ represents the flow viscosity coefficient, VT represents the tangential component of the velocity, and r represents the normal radius.

In the present disclosure, the μ may refer to the blood viscosity coefficient of the human body. Human blood is a non-Newtonian fluid. Therefore, theoretically, this blood viscosity coefficient should be a variable (non-constant). This value is not only related to the parameters of the blood such as the hematocrit and plasma viscosity, etc., but also will change with the change of the velocity gradient. Sometimes this effect is very small. When doing an approximate calculation, a specific constant may also be used as the blood viscosity coefficient for WSS calculations. For example, when calculating the WSS of the carotid artery, an average blood viscosity coefficient may be used, such as 0.0035 Pascal second (Pa·s), which may also be expressed in units of centipoise (cP), where 0.0035 Pa·s=3.5 cP. This value depends on people, and will vary with age and gender. Even for the same person, this value may be different when having different flow velocities. This value may also be measured by the falling ball method. In practical applications, a default value given by the system may be used. If the default value is considered to be inaccurate, a new value may be manually inputted. For example, the user may input a new human blood viscosity coefficient value through the input device 50.

In some embodiments, the vascular wall shear index may further include an oscillatory shear index (OSI), and the processor 40 may calculate the oscillatory shear index based on an integral of the wall shear stress within a cardiac cycle T. The oscillatory shear index can measure the condition of the wall shear stress in a cardiac cycle. Therefore, the oscillatory shear index may change with the change of the cardiac cycle. When displaying the oscillatory shear index, the oscillatory shear index displayed on the interface may change with the change of the cardiac cycle, thereby enabling the user to understand the change of the oscillatory shear index in the entire observation period. For example, the oscillatory shear index may be calculated according to the absolute value of the integral of the wall shear stress in one cardiac cycle T and the integral of the absolute value of the wall shear stress in one cardiac cycle T.

The processor 40 may further be configured to display the particle jet velocities at the multiple points in the vessel on the ultrasonic image after obtaining the particle jet velocities of the multiple points in the vessel according to the echo signals.

In some embodiments, when the vascular wall shear index includes the velocity gradient, the wall shear stress and/or the oscillatory shear index, the processor 405 may control the display device 200 to display the ultrasonic image and the vascular wall shear index, which may include: controlling the display device 200 to display the velocity gradient, the wall shear stress and/or the oscillatory shear index of the vascular wall at at least one measurement position separately or simultaneously through a map.

The processor 40 may display the velocity gradient value of the vascular wall at the measurement position, the map of the wall shear stress value over time, and/or the value and/or map of the oscillatory shear index value in different cardiac cycles. Alternatively, the processor 40 may switch between displaying the maps of the velocity gradient values, the wall shear stress values, and/or the oscillatory shear index values of the vascular wall at multiple measurement positions at current time.

Figure 5:
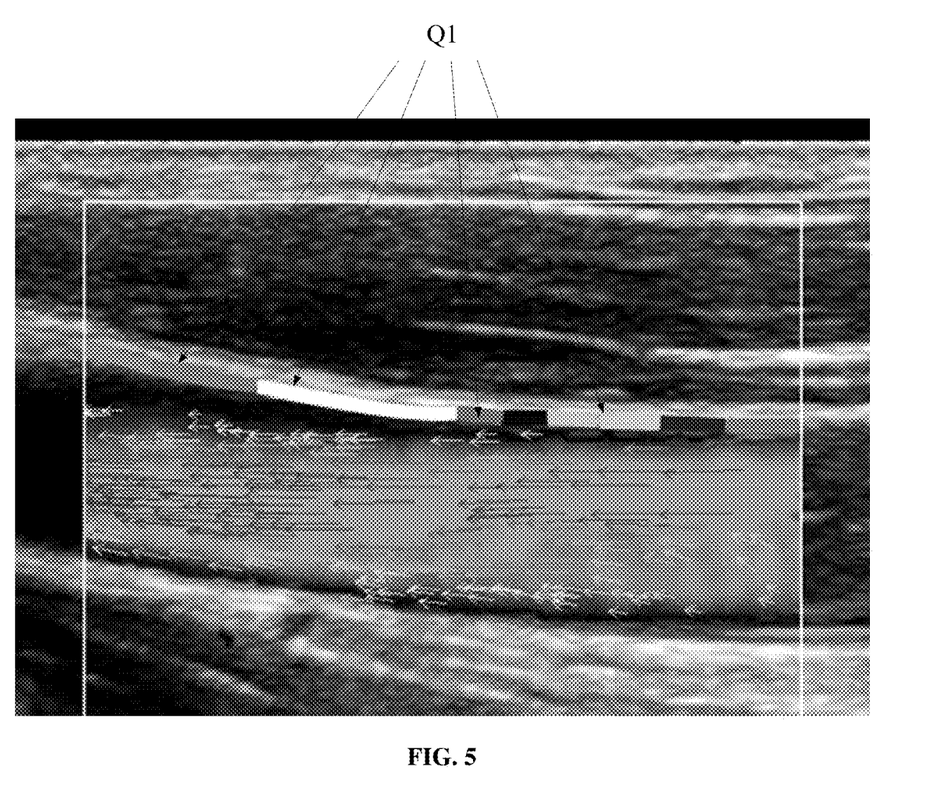
FIG. 5 is a schematic diagram of a velocity gradient value, a wall shear stress value and/or an oscillation shear index value in one embodiment of the present disclosure.

Reference may be made to FIG. 5, which is a schematic diagram of the maps of the velocity gradient value, the wall shear stress value and/or the oscillatory shear index value. As shown in FIG. 5, there may be multiple segment regions Q1 on the vessel which represent different values. Such values may be the values of the velocity gradient, the WSS or the OSI. Similarly, the lower wall of the vascular wall may also be displayed. The maps on the vascular wall may be continuously updated and changed over time. It may also be possible to manually extract the velocity gradient at any position on the vascular wall, the curve of the WSS over time and the value of the OSI at different cardiac cycles. In some embodiments, the colors of the regions Q1 on the vessel may be different according to the values of the velocity gradient, the WSS or the OSI. Due to the requirements of the drawings in the application document, the colors are not shown in the figure. In some embodiments, the colors of the regions Q1 on the vessel may be the same, while the color depth may vary according to the values of the velocity gradients, the WSS or the OSI.

The processor 40 may further be configured to display the position with the maximum, minimum or average velocity gradient or wall shear stress in a time period or one cardiac cycle and the position with the maximum or minimum or average oscillatory shear index in multiple cardiac cycles in the vascular wall at the at least one measurement position, and display the values of the corresponding maximum or minimum or average velocity gradient, wall shear stress and oscillatory shear index.

The processor 40 may further be configured to determine a position of the carotid bifurcation according to the ultrasonic image. The display control module 405 may further be configured to display the velocity gradient, the wall shear stress and/or the oscillatory shear index at the position of the carotid bifurcation.

Figure 6:
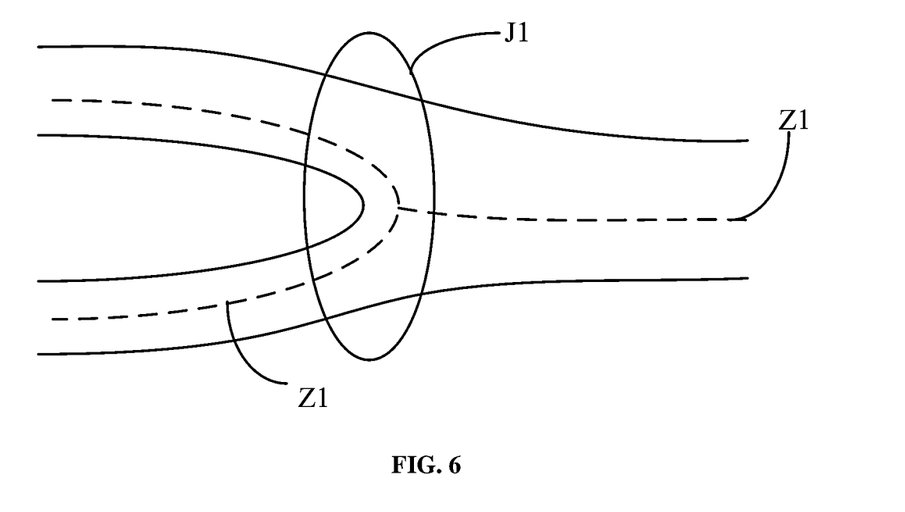
FIG. 6 is a schematic diagram of a carotid bifurcation position in one embodiment of the present disclosure.

Reference may be made to FIG. 6, which is a schematic diagram of the position of the carotid bifurcation. Specifically, the processor 40 may determine center lines Z1 of the vessels in the region of interest according to the ultrasonic image, and determine a position where multiple center lines Z1 intersect to be the position of the carotid bifurcation J1.

In the embodiment of the present disclosure, it will not be limited to displaying and marking the velocity gradient, the wall shear stress and/or the oscillatory shear index at the carotid bifurcation, and may also be applied to other vessel intersections. For example, in one embodiment, the processor may also determine the position of the bifurcation of the vessels according to the ultrasonic image, and display the velocity gradient, the wall shear stress and/or the oscillatory shear index at the bifurcation of the vessel. Furthermore, the processor may determine the center lines of the vessel in the region of interest according to the ultrasonic image, and determine a position where multiple center lines intersect to be the position of the bifurcation of the vessels.

In the present disclosure, the ultrasonic image may be a two-dimensional image or a three-dimensional image.

In some embodiments, the processor 40 may automatically generate an index mark after calculating the vascular wall shear index at the measurement position according to the particle jet velocities at the multiple points near the measurement position, and display the index mark corresponding to the measurement position at the measurement position on the vascular wall in the ultrasonic image. The attribute of the index mark may correspond to the calculated value of the vascular wall shear index. The attribute may be the length, color or the like of the index mark corresponding to the calculated value.

As shown in FIG. 1, the ultrasonic imaging apparatus 100 may further include a memory 60. In some embodiments, the memory 60 may stores program instructions. The processor 40 may implement the functions described above by calling and executing the program instructions stored in the memory 60.

In some embodiments, a computer-readable storage medium may further be provided. The computer-readable storage medium may store program instruction which can be called by the processor 40 to implement the functions described above. In the present disclosure, the computer-readable storage medium may be the memory 60. The memory 60 may be a storage device such as a memory card, a solid-state memory, a hard disk, and an optical disc, etc.

The processor 40 may be a central processing unit, a microprocessor, a single-chip microcomputer, a digital signal processor, or the like. The input device 50 may be a mouse, a touch pad, or the like. In some embodiments, in the case that the display device 200 is a display screen integrated in the ultrasonic imaging apparatus 100 and the input device 50 is a touch panel, the input device 50 and the display device 200 may be integrated into a touch display screen.

Figure 7:
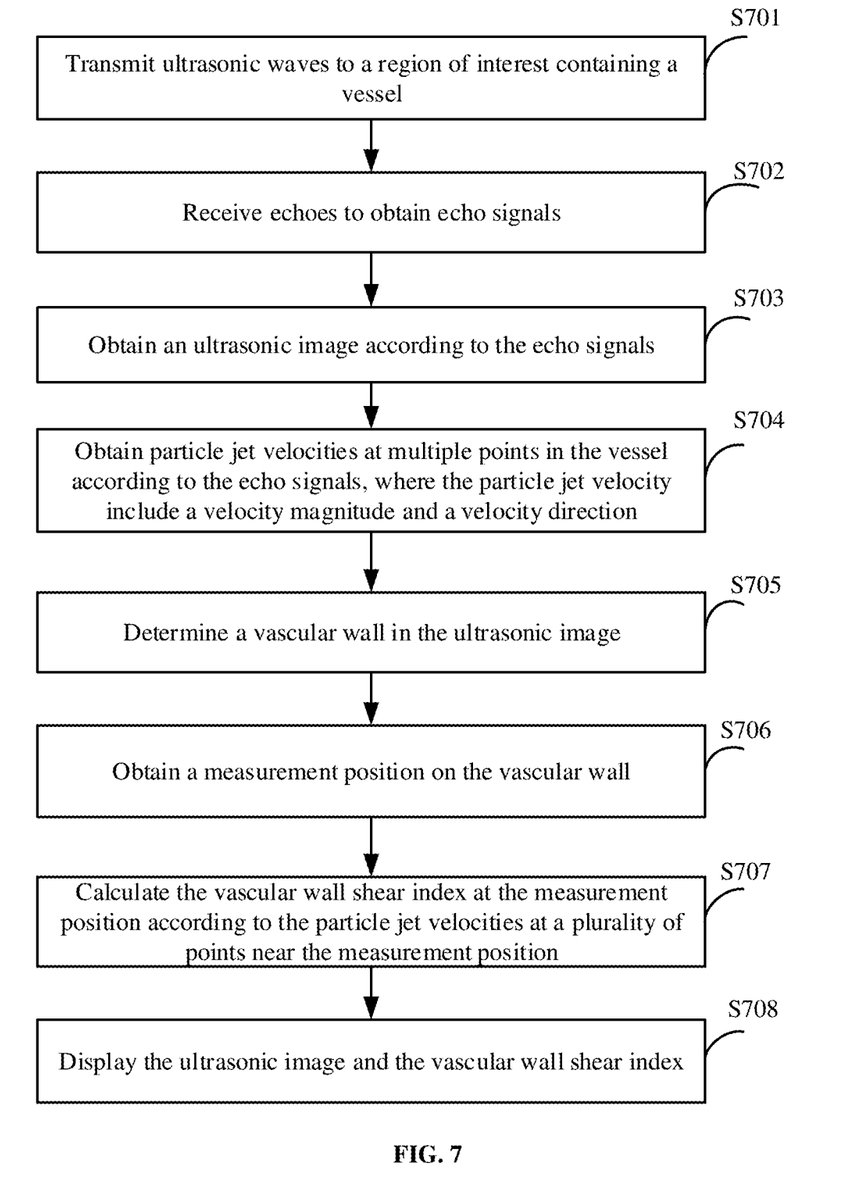
FIG. 7 is a flowchart of a method for detecting a vascular wall shear index using ultrasonic waves in one embodiment of the present disclosure.

Reference may be made to FIG. 7, which is a flowchart of a method for detecting the vascular wall shear index using ultrasonic waves in one embodiment of the present disclosure. The steps in the method will not be limited to the order in the figure, and those skilled in the art can change the execution order as required. The method may be applied to the ultrasonic imaging apparatus 100. The method may include the following step.

Ultrasonic waves may be transmitted to the region of interest containing the vessel (S701).

In some embodiments, the step S701 may include: transmitting multiple first ultrasonic waves with multiple steering angles to the scanning target in a multiple-steering angle transmitting mode. In some embodiments, the step S701 may further include: transmitting a second ultrasonic wave to the region of interest containing the vessel. The first ultrasonic waves may be transmitted before or after the second ultrasonic wave.

The ultrasonic echo waves may be received to obtain echo signals (S702).

The ultrasonic image may be obtained according to the echo signals (S703).

In some embodiments, the step S703 may include: obtaining the ultrasonic image according to second echo signals obtained in response to the second ultrasonic wave, where the first ultrasonic wave is different from the second ultrasonic wave.

The particle jet velocities at multiple points in the vessel may be obtained according to the echo signals, where the particle jet velocity may include the magnitude and the direction of the velocity (S704).

In some embodiments, the step S704 may include: respectively obtaining the velocity components of each point of the multiple points in the multiple steering angles according to the first echo signals of the first ultrasonic waves in the multiple steering angles, and respectively recovering the particle jet velocity from the velocity components in the multiple steering angles at each point of the multiple points, thereby obtaining the particle jet velocities at the multiple points.

The vascular wall in the ultrasonic image may be determined (S705). In some embodiments, the step S705 may include: determining the vascular wall at the vessel detection position in response to the vascular wall identifier added on the ultrasonic image.

In other embodiments, the step S705 may include: determining an area in the ultrasonic image where the brightness is higher than a preset brightness threshold, and determining such area where the brightness is higher than a preset brightness threshold to be the vascular wall. In still other embodiments, the step S705 may include: calculating the flow energy at the vessel detection position, searching for the edge of the flow energy, and determining the area in the ultrasonic image in which the brightness is higher than the preset brightness threshold and which is located at the edge of the flow energy and determining such area to be the vascular wall.

The searching for the edge of the flow energy may include: comparing the flow energy with the energy threshold, and determining the position where the flow energy is lower than the energy threshold to be the edge of the flow energy.

The measurement position on the vascular wall may be obtained (S706). The measurement position may be determined according to the vascular wall identifier added to the ultrasonic image. For example, it may be determined that the area including at least the vascular wall identifier is the measurement position.

The vascular wall shear index at the measurement position may be calculated according to the particle jet velocities at the multiple points near the measurement position (S707).

In some embodiments, the step S707 may include: determining the tangential direction of the vascular wall at the measurement position, obtaining the particle jet velocities at the multiple points near the measurement position, calculating the velocity components in the tangential direction of the particle jet velocities at the multiple points, and obtaining the vascular wall shear index at the measurement position according to the calculated plurality of velocity components.

In some embodiments, the determining the tangential direction of the vascular wall at the measurement position may include: in response to an adjustment to the vascular wall identifier, determining the direction of a tangential marker used to indicate the tangential direction in the adjusted vascular wall identifier to be the tangential direction of the vascular wall.

In some embodiments, the vascular wall shear index may include the velocity gradient. The obtaining the vascular wall shear index at the measurement position according to the calculated plurality of velocity components may include: obtaining the derivative of the plurality of velocity components with the normal radius of the vascular wall at the current measurement position to obtain the velocity gradient.

In some embodiment, the velocity gradient of the vascular wall may be calculated according to a formula $$\left.\frac{\partial v_T}{\partial r}\right|_{r=R}.$$

In this formula, VT represents the velocity component, i.e. the component of the velocity in the tangential direction of the vascular wall. The velocity gradient may be obtained by deriving the velocity component at the normal radius r=R of the vascular wall.

In some embodiments, the vascular wall shear index may include the wall shear stress, and the obtaining the vascular wall shear index at the measurement position according to the calculated plurality of velocity components may include: calculating the product of the flow viscosity coefficient and the obtained velocity gradient to obtain the wall surface shear stress.

Specifically, the wall shear stress in the vascular wall shear index may be calculated according to a formula $$\tau = \mu \left.\frac{\partial v_T}{\partial r}\right|_{r=R},$$

where τ represents the WSS (Wall Shear Stress), μ represents the flow viscosity coefficient, VT represents the tangential component of the velocity, and r represents the normal radius.

In some embodiments, the vascular wall shear index may include the oscillatory shear index (OSI), and the obtaining the vascular wall shear index at the measurement position according to the calculated plurality of velocity components may include: calculating the oscillatory shear index according to the absolute value of the integral of the wall shear stress in one cardiac cycle T and the integral of the absolute value of the wall shear stress in one cardiac cycle T. Specifically, the oscillatory shear index may be calculated according to a formula $$OSI = 0.5 \times \left(1 - \frac{\left|\int_0^T \tau dt\right|}{\int_0^T |\tau| dt}\right),$$

where τ represents the WSS (Wall Shear Stress).

The ultrasonic image and the vascular wall shear index may be displayed (S508). In some embodiments, the vascular wall shear index may include the velocity gradient, the wall shear stress and/or the oscillatory shear index, and the step S508 may include: displaying the velocity gradient, the wall shear stress and/or the oscillatory shear index of the vascular wall at at least one measurement position separately or simultaneously through the map.

The "displaying the velocity gradient, the wall shear stress and/or the oscillatory shear index of the vascular wall at at least one measurement position separately or simultaneously through the map" may further include: displaying the map of the velocity gradient values, the wall shear stress values and/or the oscillatory shear index values of the vascular wall at a measurement position over time, or displaying the map of the velocity gradient values, the wall shear stress values and/or the oscillatory shear index values at multiple measurement positions at the current moment.

In some embodiments, the "displaying the velocity gradient, the wall shear stress and/or the oscillatory shear index of the vascular wall at at least one measurement position separately or simultaneously the map" may further include: displaying the position in the vascular wall at the at least one measurement position with the maximum or minimum velocity gradient, wall shear stress or oscillatory shear index, and the value of the corresponding maximum or minimum velocity gradient, wall shear stress or oscillatory shear index.

In some embodiments, the method for detecting the vascular wall shear index using ultrasonic waves may further include, after the step S704, displaying the particle jet velocities at the multiple points in the vessel on the ultrasonic image. As shown in FIG. 3 and FIG. 5, multiple arrows may be superimposed on the ultrasonic image, where the lengths of the arrows may represent the magnitude of the velocities and the pointing directions of the arrows may represent the direction of the velocities. Other velocity indicators than the arrows indicating the particle jet velocities at the multiple points in the vessel may also be used, such as dots (the sizes of the dots may represent the magnitude of the velocities and the flowing directions of the dots may represent the directions of the velocities), triangular boxes (the area of the triangle boxes may represent the magnitude of the velocities and the vertexes of the triangle boxes may represent the directions of the velocities) and so on.

In some embodiments, the method for detecting the vascular wall shear index using ultrasonic waves may further include: determining the position of the carotid bifurcation according to an ultrasonic image, and the velocity gradient, the vascular wall shear stress and/or the oscillatory shear index at the position of the carotid bifurcation.

The step of "determining the position of the carotid bifurcation according to the ultrasonic image" may include: determining the center lines of the vessels in the region of interest according to the ultrasonic image, and determining the position where multiple center lines intersect to be the position of the carotid bifurcation.

Figure 8:
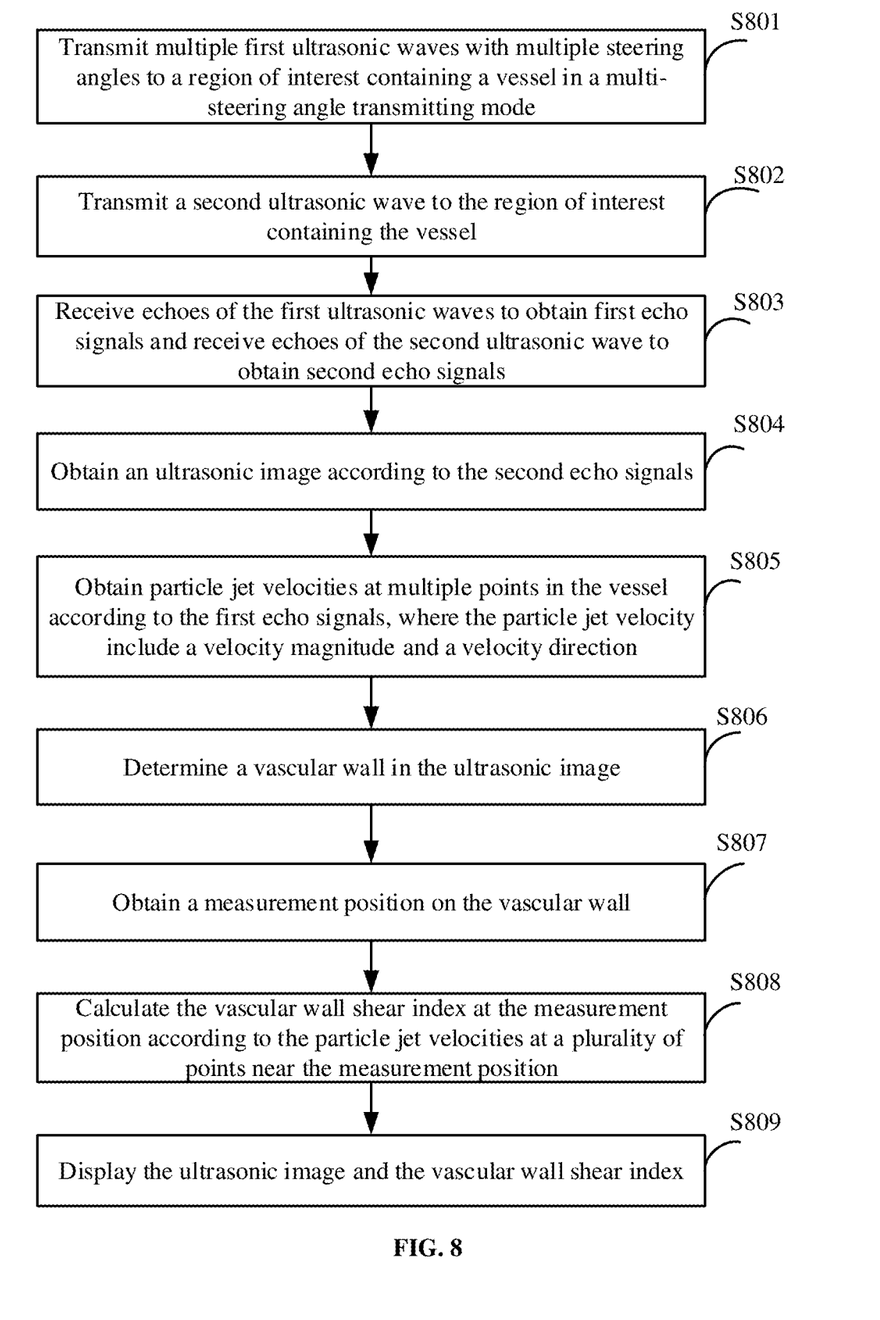
FIG. 8 is a flowchart of a method for detecting a vascular wall shear index using ultrasonic waves in another embodiment of the present disclosure.

Reference may be made to FIG. 8, which is a flowchart of a method for detecting the vascular wall shear index using ultrasonic waves in another embodiment of the present disclosure. In the another embodiment, the method may include the following steps.

Multiple first ultrasonic waves with multiple steering angles may be transmitted to the region of interest containing the vessel in a multi-steering angle transmitting mode (S801).

A second ultrasonic wave may be transmitted to the region of interest containing the vessel (S802). The first ultrasonic wave may be different from the second ultrasonic wave.

The echoes of the first ultrasonic waves may be received to obtain the first echo signals, and the echoes of the second ultrasonic wave may be obtained to obtain the second echo signals (S803).

An ultrasonic image may be obtained according to the second echo signals (S804).

The particle jet velocities at the multiple points in the vessel may be obtained according to the first echo signals, where the particle jet velocity may include the magnitude and direction of the flow velocity (S805).

The vascular wall in the ultrasonic image may be determined (S806).

The measurement position on the vascular wall may be obtained (S807).

The vascular wall shear index at the measurement position may be calculated according to the particle jet velocities at the multiple points near the measurement position (S808).

The ultrasonic image and the vascular wall shear index may be displayed (S809).

The steps S804-S809 above may correspond to the steps S703-S708 in FIG. 7, respectively. Regarding the details, reference may be made to the description of the steps S703-S708 in FIG. 7, which will not be described here again.

Figure 9:
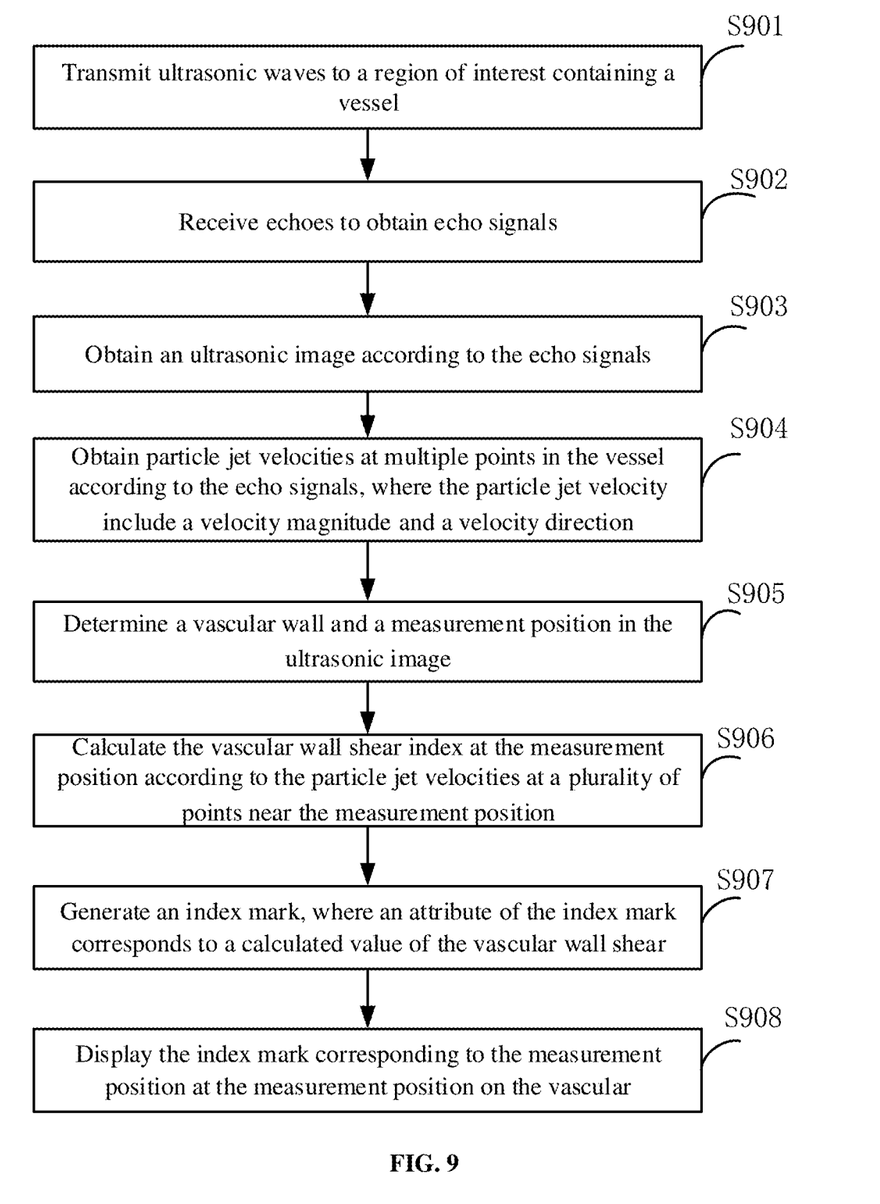
FIG. 9 is a flowchart of a method for detecting a vascular wall shear index using ultrasonic waves in another embodiment of the present disclosure.

Reference may be made to FIG. 9, which is a flowchart of a method for detecting the vascular wall shear index using ultrasonic waves in another embodiment of the present disclosure. In this embodiment, the method may include the following steps.

The ultrasonic waves may be transmitted to the region of interest containing the vessels (S901).

The echoes of the ultrasonic waves may be received to obtain the echo signals (S902). An ultrasonic image may be obtained according to the echo signals (S903).

The particle jet velocities at the multiple points in the vessel may be obtained according to the echo signals, where the particle jet velocity may include the magnitude and direction of the flow velocity (S904).

The vascular wall and the measurement position in the ultrasonic image may be determined (S905).

The vascular wall shear index at the measurement position may be calculated according to the particle jet velocities at the multiple points near the measurement position on the vascular wall (S906).

An index mark may be generated, and the attribute of the index mark may be associated with the calculated value of the vascular wall shear index (S907). Specifically, the attribute of the index mark include, but not limited to, length, color, or the like. The index mark having a corresponding length, color or other attributes may be generated according to the vascular wall shear index.

The index mark corresponding to the measurement position may be displayed at the measurement position on the vascular wall (S908).

The steps S901-S904 in this embodiment may correspond to the steps S701-S704 in FIG. 7, the step S905 may correspond to the steps S705-S706 in FIG. 7, and the step S906 may correspond to the step S707 in FIG. 7. Regarding the details, reference may be made to the description of the steps in FIG. 7, which will not be described here again.

The program instructions stored in the memory 60/computer-readable storage medium may be called and executed by the processor 40 to implement the steps in the method shown in any one of FIGS. 7-9.

Therefore, in the present disclosure, the vascular wall shear index including the velocity gradient, the wall shear stress and the oscillatory shear index at the vascular wall may be accurately detected at a lower cost.

The embodiments of the present disclosure have been described above. It should be noted that, for those ordinarily skilled in the art, several improvements and modifications may be made without departing from the principles of the present disclosure, which shall also fall into the protection scope of the present disclosure.

What is claimed is:

1. An ultrasonic imaging apparatus, comprising:
a probe;
a transmitting circuit configured to excite the probe to transmit ultrasonic waves to a region of interest containing a vessel;
a receiving circuit configured to receive echo signals generated after the transmitting of the ultrasonic waves; and
a processor configured to:
obtain an ultrasonic image of the region of interest according to the echo signals;
obtain particle jet velocities at multiple points in the vessel according to the echo signals, wherein the particle jet velocity comprises a velocity magnitude and a velocity direction;
determine a vascular wall in the ultrasonic image, and obtain a measurement position on the vascular wall;
calculate a vascular wall shear index at the measurement position according to the particle jet velocities at a plurality of points near the measurement position; and
display the ultrasonic image and the vascular wall shear index on a display device.

2. The ultrasonic imaging apparatus of claim 1, wherein, the ultrasonic waves transmitted to the region of interest containing the vessel by the probe excited by the transmitting circuit comprise multiple first ultrasonic wave with multiple steering angles transmitted in a multi-steering angle transmitting mode, and
the processor, according to first echo signals in the multiple steering angles at the multiple points received by the receiving circuit, respectively obtains velocity components in the multiple steering angles at each point of the multiple points and recovers a particle jet velocity from the velocity components in the multiple steering angles at each point of the multiple points to obtain the particle jet velocities at the multiple points.

3. The ultrasonic imaging apparatus of claim 2, wherein, the ultrasonic waves transmitted to the region of interest containing the vessel by the probe excited by the transmitting circuit further comprise a second ultrasonic wave, and the processor generates the ultrasonic image according to a second echo signal obtained by the receiving circuit receiving echoes of the second ultrasonic wave, wherein the first ultrasonic wave is different from the second ultrasonic wave.

4. The ultrasonic imaging apparatus of claim 1, wherein the processor is configured to calculate the vascular wall shear index at the measurement position according to the particle jet velocities at the plurality of points near the measurement position by:
determining a tangential direction of the vascular wall at the measurement position;
obtaining the particle jet velocities at the plurality of points near the measurement position;
calculating velocity components of the particle jet velocities at the plurality of points in the tangential direction; and
obtaining the vascular wall shear index at the measurement position according to the calculated plurality of velocity components.

5. The ultrasonic imaging apparatus of claim 4, wherein the processor is configured to determine the tangential direction of the vascular wall at the measurement position by:
in response to an adjustment to a vascular wall identifier, determining a direction of a tangential marker used to indicate the tangential direction in the adjusted vascular wall identifier to be the tangential direction of the vascular wall.

6. The ultrasonic imaging apparatus of claim 1, wherein the processor is configured to determine the vascular wall at the vessel detection position in response to a vascular wall identifier added on the ultrasonic image.

7. The ultrasonic imaging apparatus of claim 1, wherein the processor is configured to obtain an area in the ultrasonic image in which a brightness is higher than a preset brightness threshold and determine the area in which the brightness is higher than the preset brightness to be the vascular wall.

8. The ultrasonic imaging apparatus of claim 1, wherein the processor is configured to:
calculate a flow energy at a vessel detection position;
search for an edge of the flow energy; and
obtain an area in the ultrasonic image in which a brightness is higher than a preset brightness threshold and which is located at the edge of the flow energy and determine the area to be the vascular wall.

9. The ultrasonic imaging apparatus of claim 8, wherein the processor is further configured to compare the flow energy with an energy threshold and determine a position where the flow energy is lower than the energy threshold to be a position of the edge of the flow energy.

10. The ultrasonic imaging apparatus of claim 1, wherein, the vascular wall shear index comprises a velocity gradient, and the processor is configured to obtain the velocity gradient by obtaining derivatives of the plurality of velocity components with a normal radius of the vascular wall at current measurement position.

11. The ultrasonic imaging apparatus of claim 10, wherein, the vascular wall shear index further comprises a wall shear stress, and the processor is further configured to obtain the wall shear stress by calculating a product of a flow viscosity coefficient and the velocity gradient.

12. The ultrasonic imaging apparatus of claim 11, wherein, the vascular wall shear index further comprises an oscillatory shear index, and the processor is further configured to calculate the oscillatory shear index according to an integral of the wall shear stress in one cardiac cycle.

13. The ultrasonic imaging apparatus of claim 1, wherein the processor is further configured to display the particle jet velocities at the multiple points in the vessel on the ultrasonic image.

14. The ultrasonic imaging apparatus of claim 1, wherein
the vascular wall shear index comprises a velocity gradient, a wall shear stress and/or an oscillatory shear index, and
the processor displays the ultrasonic image and the vascular wall shear index on the display device by:
displaying the velocity gradient, the wall shear stress and/or the oscillatory shear index of the vascular wall at at least one measurement position separately or simultaneously through a map on the display device.

15. The ultrasonic imaging apparatus of claim 14, wherein,
the processor displays a value of the velocity gradient, a map of values of the wall shear stress over time, and/or, values and/or map of the oscillatory shear index in different cardiac cycles of the vascular wall at one measurement position; or
the processor switches between displaying maps of the velocity gradient, the wall shear stress and/or the oscillatory shear index of the vascular wall at a current moment at multiple measurement positions.

16. The ultrasonic imaging apparatus of claim 14, wherein the processor is further configured to display a position with a maximum, minimum or average velocity gradient or wall shear stress in a time period or one cardiac cycle and a position with a maximum or minimum or average oscillatory shear index in multiple cardiac cycles in the vascular wall at the at least one measurement position, and display values of the corresponding maximum or minimum or average velocity gradient, wall shear stress and oscillatory shear index.

17. The ultrasonic imaging apparatus of claim 14, wherein the processor is further configured to determine a vessel bifurcation position according to the ultrasonic image and display the velocity gradient, the wall shear stress and/or the oscillatory shear index at the vessel bifurcation position.

18. The ultrasonic imaging apparatus of claim 17, wherein the processor is further configured to determine center lines of vessels in the region of interest according to the ultrasonic image and determine a position where multiple center lines intersect to be the vessel bifurcation position.

19. A method for detecting a vascular wall shear index using ultrasonic waves, comprising:
transmitting ultrasonic waves to a region of interest containing a vessel;
receiving echoes to obtain echo signals;
obtaining an ultrasonic image according to the echo signals;
obtaining particle jet velocities at multiple points in the vessel according to the echo signals, wherein the particle jet velocity comprises a velocity magnitude and a velocity direction;
determining a vascular wall in the ultrasonic image;
obtaining a measurement position on the vascular wall;
calculating the vascular wall shear index at the measurement position according to the particle jet velocities at a plurality of points near the measurement position; and
displaying the ultrasonic image and the vascular wall shear index.

20. A method for detecting a vascular wall shear index using ultrasonic waves, comprising:
transmitting ultrasonic waves to a region of interest containing a vessel;
receiving echoes to obtain echo signals;
obtaining an ultrasonic image according to the echo signals;
obtaining particle jet velocities at multiple points in the vessel according to the echo signals, wherein the particle jet velocity comprises a velocity magnitude and a velocity direction;
determining a vascular wall and a measurement position in the ultrasonic image;
calculating the vascular wall shear index at the measurement position according to the particle jet velocities at a plurality of points near the measurement position of the vascular wall;
generating an index mark, wherein an attribute of the index mark corresponds to a calculated value of the vascular wall shear index; and
displaying the index mark corresponding to the measurement position at the measurement position on the vascular wall.

* * * * *